United States Patent
Yu et al.

(10) Patent No.: US 11,550,069 B2
(45) Date of Patent: Jan. 10, 2023

(54) DETECTOR MODULES, DETECTORS AND MEDICAL IMAGING DEVICES

(71) Applicant: Shanghai Neusoft Medical Technology Co., Ltd., Shanghai (CN)

(72) Inventors: Jun Yu, Shanghai (CN); Shuangxue Li, Shanghai (CN); Yiguang Tan, Shanghai (CN)

(73) Assignee: Shanghai Neusoft Medical Technology Co., Ltd., Shanghai (CN)

(*) Notice: Subject to any disclaimer, the term of this patent is extended or adjusted under 35 U.S.C. 154(b) by 0 days.

(21) Appl. No.: 17/014,785

(22) Filed: Sep. 8, 2020

(65) Prior Publication Data
US 2021/0072410 A1 Mar. 11, 2021

(30) Foreign Application Priority Data
Sep. 9, 2019 (CN) .......................... 201910849740.5

(51) Int. Cl.
*G01T 1/20* (2006.01)
*A61B 6/03* (2006.01)
*A61B 6/00* (2006.01)

(52) U.S. Cl.
CPC .......... *G01T 1/20181* (2020.05); *A61B 6/032* (2013.01); *A61B 6/4266* (2013.01);
(Continued)

(58) Field of Classification Search
CPC ..... A61B 6/032; A61B 6/4233; A61B 6/4266; A61B 6/4283; A61B 6/4291;
(Continued)

(56) References Cited

U.S. PATENT DOCUMENTS 4,467,342 A * 8/1984 Tower ................. H01L 25/0655
257/443
5,834,782 A * 11/1998 Schick ................. H04N 5/3415
250/370.09
(Continued)

FOREIGN PATENT DOCUMENTS

CN 1633607 A 6/2005
CN 101535836 A 9/2009
(Continued)

OTHER PUBLICATIONS

EP Partial Extended European Search Report in European Appln. No. 20195102.7, dated Feb. 4, 2021, 16 pages.
(Continued)

*Primary Examiner* — Dani Fox
*Assistant Examiner* — Soorena Kefayati
(74) *Attorney, Agent, or Firm* — Fish & Richardson P.C.

(57) ABSTRACT

Detector modules, detectors and medical imaging devices are provided. One of the detector modules includes: a support and a plurality of detector sub-modules arranged on the support along an extension direction in which the support extends. Each of the detector sub-modules has a first area and a second area in the extension direction. A detecting device is disposed in the first area, and a functional module is disposed in the second area. The functional module is electrically connected to the detecting device for receiving an electrical signal from the detecting device. The plurality of detector sub-modules includes a first detector sub-module and a second detector sub-module that are arranged adjacent to each other in the extension direction, and the first area of the first detector sub-module at least partially overlaps with the second area of the second detector sub-module.

17 Claims, 5 Drawing Sheets

(52) U.S. Cl.
CPC .......... *A61B 6/4283* (2013.01); *A61B 6/4435* (2013.01); *A61B 6/4488* (2013.01)

(58) Field of Classification Search
CPC ... A61B 6/4435; A61B 6/4488; G01T 1/2018; G01T 1/20181; G01T 1/20182; G01T 1/2985
See application file for complete search history.

(56) References Cited

U.S. PATENT DOCUMENTS

| | | | | |
|---|---|---|---|---|
| 6,207,944 | B1* | 3/2001 | Spartiotis | H01L 27/14601 250/214 R |
| 6,748,049 | B1* | 6/2004 | Yamamoto | H04N 5/325 378/62 |
| 6,847,040 | B2* | 1/2005 | Strommer | H04N 5/3743 348/E5.086 |
| 8,098,795 | B2* | 1/2012 | Nowak | G01T 1/00 378/62 |
| 8,461,543 | B2* | 6/2013 | Nishino | A61B 6/548 250/370.08 |
| 9,239,392 | B2* | 1/2016 | Gemma | G01T 1/2006 |
| 9,955,930 | B2* | 5/2018 | Steadman Booker | G01T 1/243 |
| 10,695,024 | B2* | 6/2020 | Miyamoto | G06T 5/009 |
| 2002/0018543 | A1* | 2/2002 | Danielsson | G01T 1/24 378/154 |
| 2002/0130266 | A1* | 9/2002 | Kyyhkynen | G01T 1/243 250/370.09 |
| 2003/0155516 | A1* | 8/2003 | Spartiotis | G01T 1/2928 250/370.09 |
| 2004/0200971 | A1* | 10/2004 | De Keyser | G01N 23/04 378/98.8 |
| 2006/0219926 | A1* | 10/2006 | Shoji | A61B 6/5235 250/370.09 |
| 2007/0069111 | A1* | 3/2007 | Spahn | H01L 27/14663 250/370.11 |
| 2008/0135765 | A1* | 6/2008 | Vydrin | G01T 1/1642 250/359.1 |
| 2009/0121146 | A1* | 5/2009 | Luhta | H01L 27/14661 250/370.11 |
| 2010/0150305 | A1 | 6/2010 | Nowak et al. | |
| 2011/0233415 | A1* | 9/2011 | Nakatsugawa | G01T 1/2985 250/370.08 |
| 2012/0087465 | A1* | 4/2012 | Ikhlef | A61B 6/00 378/19 |
| 2012/0133054 | A1* | 5/2012 | Tkaczyk | G01T 1/243 438/57 |
| 2013/0153774 | A1* | 6/2013 | Hughes | G01T 1/1644 250/366 |
| 2014/0163368 | A1* | 6/2014 | Rousso | A61B 6/4258 600/436 |
| 2014/0233690 | A1* | 8/2014 | Hashimoto | H01L 27/14636 250/366 |
| 2015/0049855 | A1 | 2/2015 | Funk et al. | |
| 2015/0245807 | A1* | 9/2015 | Tajima | A61B 6/5294 378/98 |
| 2016/0209521 | A1* | 7/2016 | Jakubek | G01T 1/243 |
| 2016/0320495 | A1* | 11/2016 | Ying | G01T 1/2018 |
| 2017/0059721 | A1* | 3/2017 | Simanovsky | G01T 1/243 |
| 2017/0090046 | A1* | 3/2017 | Danielsson | A61B 6/4266 |
| 2019/0120977 | A1* | 4/2019 | Jacobs | G01T 1/2018 |
| 2019/0223816 | A1* | 7/2019 | Bouhnik | A61B 6/544 |
| 2019/0350545 | A1* | 11/2019 | Ikhlef | A61B 6/4233 |
| 2020/0121270 | A1* | 4/2020 | Wojcik | A61B 6/0407 |

FOREIGN PATENT DOCUMENTS

| | | |
|---|---|---|
| CN | 102204826 A | 10/2011 |
| CN | 102365562 A | 2/2012 |
| CN | 102440794 A | 5/2012 |
| CN | 104023641 A | 9/2014 |
| CN | 104887255 A | 9/2015 |
| CN | 106255900 A | 12/2016 |
| CN | 108836376 A | 11/2018 |
| CN | 109106391 A | 1/2019 |
| CN | 208808503 U | 5/2019 |
| EP | 2578149 A2 | 4/2013 |
| GB | 2332608 | 6/1999 |
| JP | 2000292546 A | 10/2000 |
| JP | 2006263339 A | 10/2006 |
| JP | 2012040140 A | 3/2012 |
| JP | 2012179373 A | 9/2012 |
| JP | 2014062898 | 4/2014 |
| JP | 2015104667 | 6/2015 |
| JP | 2016531296 | 10/2016 |
| WO | WO2017200507 A1 | 11/2017 |
| WO | WO2019047054 A1 | 3/2019 |

OTHER PUBLICATIONS

State Intellectual Property Office of the People's Republic of China, Office Action and Search Report Issued in Application No. 2019108497405, dated May 12, 2020, 20 pages, (Submitted with Machine Translation).
State Intellectual Property Office of the People's Republic of China, Office Action and Search Report Issued in Application No. 2019108497405, dated Jul. 30, 2020, 20 pages, (Submitted with Machine Translation).
JP Office Action in Japanese Appln. No. 2020-151241, dated Aug. 24, 2021, 8 pages (with Machine Translation).
Decision of Reexamination in Chinese Application No. 201910849740. 5, dated Jul. 4, 2022, 26 pages (with English Machine translation).
Office Action in Chinese Appln. No. 201910849740.5, dated Aug. 10, 2022, 30 pages (with English Machine translation).
JP Decision of Refusal in Japanese Application No. 2020-151241, dated Apr. 12, 2022, 10 pages (with Machine Translation).
Office Action in Chinese Appln. No. 2019108497405, dated Nov. 16, 2022, 20 pages (Submitted with Machine Translation).

* cited by examiner

DETECTOR MODULES, DETECTORS AND MEDICAL IMAGING DEVICES

CROSS REFERENCE TO RELATED APPLICATIONS

This application claims priority to Chinese Patent Application No. 201910849740.5 entitled "DETECTOR MODULES, DETECTORS AND MEDICAL IMAGING DEVICES" filed on Sep. 9, 2019, the entire content of which is incorporated herein by reference.

TECHNICAL FIELD

The present disclosure relates to detector modules, detectors, and medical imaging devices.

BACKGROUND

With the continuous development of medical practices, more and more medical devices are used to assist in medical diagnosis or treatment. For example, a Computed Tomography (CT) device is used to detect human diseases. The CT device can use a CT detector to detect X-rays passing through a human body and convert the received optical signals into electrical signals.

However, in a typical detector, a large gap can be formed between respective detecting devices of adjacent detector sub-modules due to limitations by functional modules in the detector sub-modules, such that discontinuous scanning data can be formed for a scanned part. Discontinuous scanning data can result in an incomplete inspection range.

SUMMARY

The present disclosure provides detector modules, detectors, and medical imaging devices.

According to a first aspect of the embodiments of the present disclosure, a detector module is provided, including: a support extending in an extension direction a plurality of detector sub-modules arranged on the support in the extension direction. Each of the detector sub-modules has a first area and a second area in the extension direction, a detecting device being disposed in the first area, a functional module being disposed in the second area. The functional module is electrically connected to the detecting device for receiving an electrical signal from the detecting device. The plurality of detector sub-modules includes a first detector sub-module and a second detector sub-module that are arranged adjacent to each other in the extension direction, the first area of the first detector sub-module at least partially overlapping with the second area of the second detector sub-module.

In some embodiments, the first area of the first detector sub-module completely covers the second area of the second detector sub-module.

In some embodiments, the plurality of detector sub-modules are arranged in parallel to each other in a stacking direction in which the plurality of detector sub-modules are stacked.

In some embodiments, the first detector sub-module is inclined with respect to the second detector sub-module.

In some embodiments, each pair of detector sub-modules of the plurality of detector sub-modules are arranged symmetrical to each other in the extension direction.

In some embodiments, at least two of the plurality of detector sub-modules are arranged asymmetrical to each other in the extension direction.

In some embodiments, the plurality of detector sub-modules include a third detector sub-module and a fourth detector sub-module of the plurality of detector sub-modules that are located at a bottom layer in a stacking direction in which the plurality of detector sub-modules are stacked, the first area of the third detector sub-module and the first area of the fourth detector sub-module are joined to each other.

In some embodiments, at least one of the plurality of detector sub-modules is stacked at least partially on the third detector sub-module sequentially in a direction from the first area of the third detector sub-module to the second area of the third detector sub-module.

In some embodiments, at least one of the plurality of detector sub-modules is stacked at least partially on the fourth detector sub-module sequentially in a direction from the first area of the fourth detector sub-module to the second area of the fourth detector sub-module.

In some embodiments, each of the plurality of detector sub-modules further includes a shield disposed over the functional module in the second area of the detector sub-module.

In some embodiments, each of the plurality of detector sub-modules further includes a thermally conductive adhesive disposed between the functional module and the shield.

In some embodiments, each of the detector sub-modules further includes a thermal fin, the thermal fin and the plurality of detector sub-modules are respectively disposed on opposite sides of the support.

In some embodiments, at least part of the thermal fin is provided with a gradually increasing heat dissipation area in a heat dissipation wind direction.

In some embodiments, each of the plurality of detector sub-module includes a substrate having a first part located in the first area of the detector sub-module and a second part located in the second area of the detector sub-module. The detecting device is disposed on the first part of the substrate, and the functional module is disposed on the second part of the substrate, and the substrate is configured to electrically connect the functional module to the detecting device and transmit the electrical signal generated by the detecting device to the functional module.

In some embodiments, the detecting device includes a photodiode array and a scintillation crystal array, and the functional module includes an analog-to-digital converter and a connector.

In some embodiments, each of the plurality of detector sub-module includes a substrate having a first part located in the first area of the detector sub-module and a second part located in the second area of the detector sub-module. The photodiode array is disposed on the first part of the substrate, and the scintillation crystal array is disposed on the photodiode array. The analog-to-digital converter and the detecting device are disposed on a same side of the substrate and electrically connected to each other. The analog-to-digital converter and the connector are disposed on opposite sides of the second part of the substrate and are in communication connection via the substrate.

According to a second aspect of the embodiments of the present disclosure, a detector is provided, including: a housing and a plurality of detector modules arranged in parallel on the housing, each of the detector modules including a support extending in an extension direction and a plurality of detector sub-modules arranged on the support along the extension direction. The plurality of detector modules are arranged in parallel in a stacking direction. The extension direction and the stacking direction are perpendicular to each other and are both perpendicular to a direction in which rays are received. Each of the detector submodules has a first area and a second area in the extension direction, a detecting device being disposed in the first area, a functional module being disposed in the second area. The functional module is electrically connected to the detecting device for receiving an electrical signal from the detecting device. The plurality of detector sub-modules includes a first detector sub-module and a second detector sub-module that are arranged adjacent to each other in the extension direction, the first area of the first detector sub-module at least partially overlapping with the second area of the second detector sub-module.

According to a third aspect of the embodiments of the present disclosure, a medical imaging device is provided, including: a scanner gantry formed with an opening for receiving an object to be scanned; a radiation source for emitting rays to the object; and a detector configured to receive the rays attenuated through the object and convert the attenuated rays into electrical signals,. The detector and the radiation source are disposed respectively on opposite sides of the opening of the scanner gantry. The detector includes a housing and a plurality of detector modules arranged in parallel on the housing. Each of the detector modules includes: a support extending in an extension direction and a plurality of detector sub-modules arranged on the support along the extension direction. The plurality of detector modules are arranged in parallel in a stacking direction. The extension direction and the stacking direction are perpendicular to each other and are both perpendicular to a direction in which rays are received. Each of the detector sub-modules has a first area and a second area in the extension direction, a detecting device being disposed in the first area, a functional module being disposed in the second area. The functional module is electrically connected to the detecting device for receiving an electrical signal from the detecting device. The plurality of detector sub-modules includes a first detector sub-module and a second detector sub-module that are arranged adjacent to each other in the extension direction, the first area of the first detector sub-module at least partially overlapping with the second area of the second detector sub-module.

In some embodiments of the present disclosure, a first area where a detecting device of a detector sub-module is disposed at least partially overlaps with a second area of another detector sub-module. Thus, a gap between respective detecting devices in adjacent detector sub-modules can be reduced or eliminated, thereby obtaining relatively complete scanning data of a scanned part and improving the accuracy of diagnosis result.

It should be understood that the above general description and the following detailed description are only exemplary and explanatory and are not intended to limit the present disclosure.

DETAILED DESCRIPTION

Hereinafter, some embodiments of the present disclosure will be described in detail with reference to the drawings. In the case of no conflict, the following embodiments and features in the embodiments can be combined with each other.

Figure 1A:
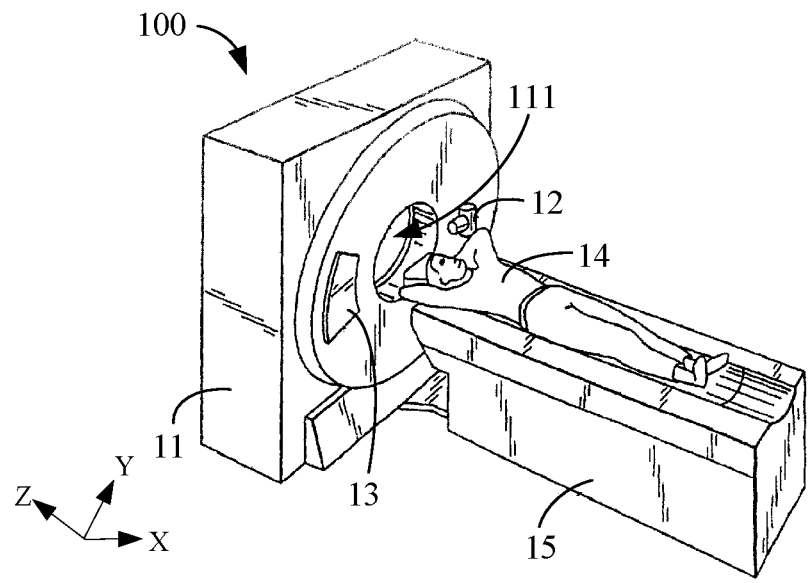
FIG. 1A illustrates a schematic diagram of a medical imaging device according to one or more embodiments of the present disclosure.

FIG. 1A illustrates a schematic diagram of a medical imaging device 100 according to one or more embodiments of the present disclosure. The medical imaging device 100 can be a CT device. The imaging device 100 includes a scanner gantry 11, a radiation source 12 and a detector 13. The scanner gantry 11 is formed with an opening 111 for receiving an object to be scanned. The radiation source 12 and the detector 13 can be oppositely disposed on two sides of the opening 111 of the scanner gantry 11. An object 14 to be scanned, such as a patient, can be placed on a platform 15 and can be moved into the opening 111 together with the platform 15. The radiation source 12 and the detector 13 can rotate relative to the scanner gantry 11 and the object 14 for scanning.

The radiation source 12 can be configured to emit rays to the object 14. The radiation source 12 can emit fan-shaped or cone-shaped ray beams, and each ray beam includes multiple rays. The radiation source 12 can emit the ray beams from a focal point of the radiation source 12 to the object 14. The radiation source 12 includes a bulb (not shown) and a high voltage generator (not shown). The high voltage generator provides high voltage power to the bulb, and the bulb generates radiation.

Figure 1B:
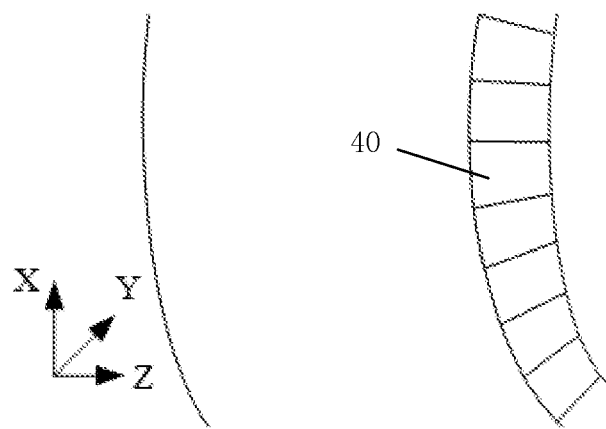
FIG. 1B illustrates a schematic diagram of an arrangement of detector modules in the medical imaging device shown in FIG. 1A.

The rays can be X-rays. The detector 13 includes a housing (not shown) and a plurality of detector modules 40. The plurality of detector modules 40 are arranged in parallel on the housing (see FIG. 1B for an exemplary arrangement of the detector modules 40). The detector 13 can be configured to detect the rays attenuated through the object 14 and convert the optical signals of the received rays into electrical signals.

Figure 2:
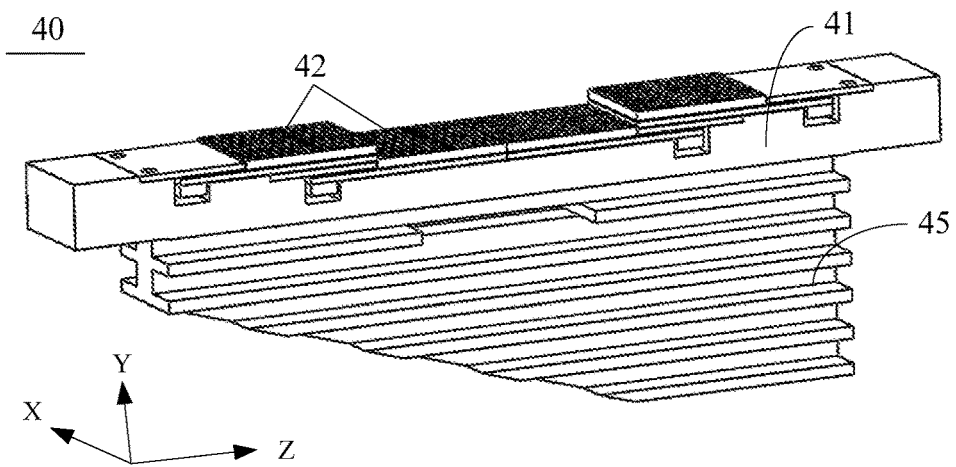
FIG. 2 illustrates a schematic structural diagram of a detector module according to one or more embodiments of the present disclosure.

As shown in FIG. 1A and FIG. 2, each detector module 40 extends along a Z direction, which is a moving direction of the platform 15. A plurality of detector modules 40 are arranged side by side along an X direction to form an arc shape. The center of a circle to which the arc belongs coincides with or near the focal point of the radiation source 12. For example, a distance between the center of the circle and the focal point is less than 1 mm, so that the rays emitted by the radiation source 12 can incident perpendicularly on the detector modules 40 along the X direction. The housing extends along the arc in the X direction. The detector 13 includes a plurality of fans (not shown) provided on a side of the housing. The fans can be used to dissipate heat of the detector 13 to prevent the detector 13 from being too hot during operation and affecting the detection result of the detector 13.

The detector module 40 of the present disclosure can be used to detect the attenuated rays emitted from the radiation source 12 and passing through the object 14. The detector module 40 includes a support 41 and a plurality of detector sub-modules 42 disposed on the support 41 along an extension direction in which the support 41 extends. The detector sub-modules 42 can be used to detect rays passing through the object 14 and convert the received rays into electrical signals.

When the rays pass through the object 14, the rays can be attenuated by the object 14. Different tissues and structures inside the object 14 can cause different degrees of attenuation for the rays passing through the object 14, thus intensities of the rays passing through the object 14 can be different. The optical signals of the attenuated rays can be received and converted into electrical signals by the detector sub-modules 42. The electrical signals represent the intensities of the rays passing through the object 14. The electrical signals generated by each detector sub-module 42 can be proportional to the intensities of the optical signals of the received attenuated rays thereon.

Figure 4:
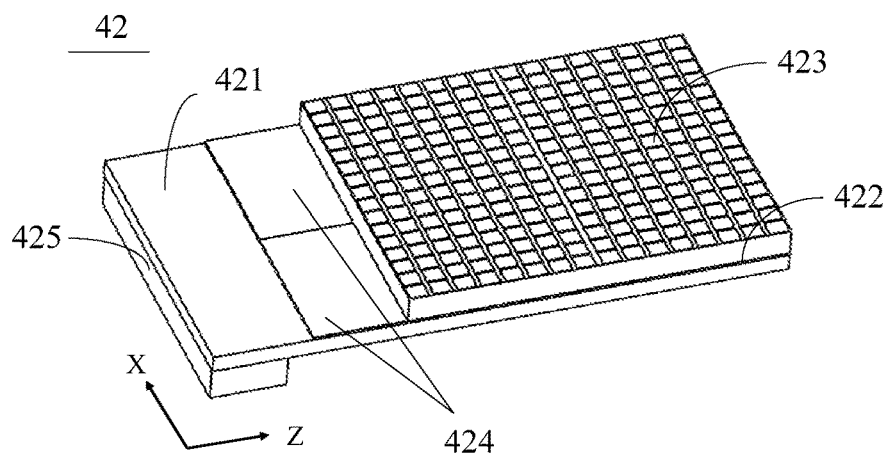
FIG. 4 illustrates a schematic structural diagram of a detector sub-module according to one or more embodiments of the present disclosure.
Figure 5:
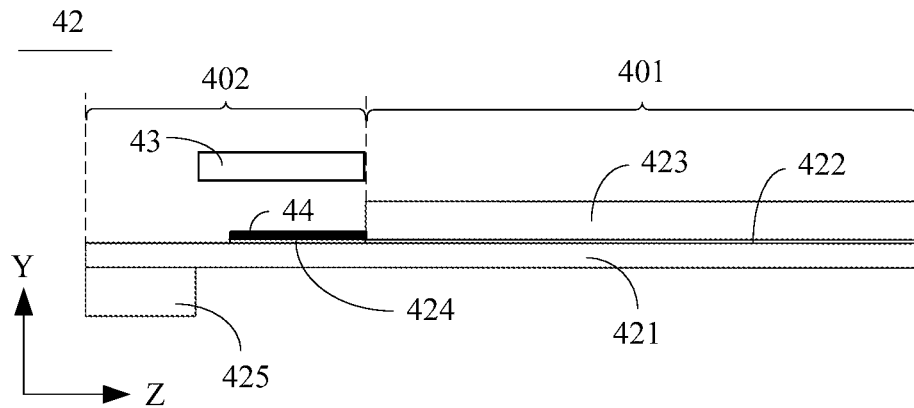
FIG. 5 illustrates a schematic cross-sectional view of a detector sub-module according to one or more embodiments of the present disclosure.

As shown in FIGS. 4 and 5, the detector sub-module 42 includes a substrate 421, a photodiode array 422, a scintillation crystal array 423, an analog-to-digital converter 424 and a connector 425. The scintillation crystal array 423 can be used to receive the attenuated rays passing through the object 14 and convert the rays into visible lights. The scintillation crystal array 423 can have a 32×16 or 16×16 matrix structure.

The photodiode array 422 can be used to obtain electrical signals based on the visible lights. The photodiode array 422 can have a matrix structure of 8×16 pixels (16 pixels in the Z direction) or 16×16 pixels. The detector sub-module 42 can be provided to have one or more photodiode arrays 422 joined along the X direction. For example, three photodiode arrays 422 with 8×16 pixels can be joined to form one detector sub-module 42 of 24×16 pixels; 4 photodiode arrays 422 with 8×16 pixels can be joined to form one detector sub-module 42 of 32×16 pixels.

The substrate 421 can serve as a carrier for carrying the scintillation crystal array 423 and the photodiode array 422, and transmitting the electrical signals generated by the photodiode array 422 to an analog-to-digital converter 424 using, for example, CMOS (Complementary Metal Oxide Semiconductor) integrated circuit. In place of circuit with connection lines and circuit board, the CMOS integrated circuit can be used to effectively shorten the signal transmission distance and reduce interference factors during the signal transmission, which is conducive to the improvement of image quality. In addition, providing offset analog-to-digital converter 424 has a lower cost.

Figure 3:
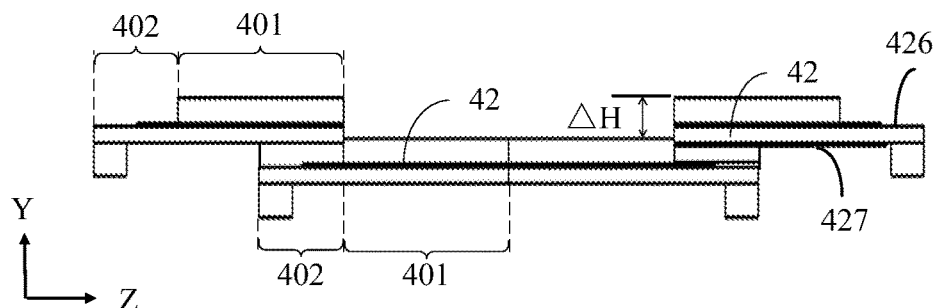
FIG. 3 illustrates a schematic partial cross-sectional view of a detector module according to one or more embodiments of the present disclosure.

As shown in FIGS. 2 to 5, the detector sub-module 42 of the present disclosure is an offset type detector sub-module. As shown in FIGS. 3 and 5, in an extension direction in which the support 41 extends, that is, the Z direction, the detector sub-module 42 includes a first area 401 provided with a detecting device and a second area 402 provided with a functional module. In some embodiments, the detecting device includes a photodiode array 422 and a scintillation crystal array 423, and the functional module includes an analog-to-digital converter 424 and a connector 425.

At least a part of the substrate 421 is located in the first area 401 and the other part of the substrate 421 is located in the second area 402. The photodiode array 422 is disposed on the part of the substrate 421 located in the first area 401, and the scintillation crystal array 423 is disposed on the photodiode array 422. The analog-to-digital converter 424 is disposed on the part of the substrate 421 located in the second area 402 and is electrically connected to the detecting device. The analog-to-digital converter 424 and the detecting device are located on a same side of the substrate 421. In a Y direction, a height of the detecting device is higher than the height of the analog-to-digital converter 424. The connector 425 is in communication connection with the analog-to-digital converter 424 via the substrate 421 and can be used to electrically connect with external devices. The connector 425 is disposed on the part of the substrate 421 located in the second area 402. The connector 425 and the analog-to-digital converter 424 are respectively disposed on the opposite sides of the substrate 421.

In the present disclosure, among the plurality of detector sub-modules 42, for a first detector sub-module 42 and a second detector sub-module 42 that are arranged adjacent to each other in the extension direction of the support, the first area 401 of the first detector sub-module at least partially overlaps with the second area 402 of the second detector sub-module.

As shown in FIG. 3, each detector sub-module 42 includes a first side surface 426 provided with a detecting device and a second side surface 427 opposite to the first side surface. The connector 425 is disposed on the second side surface 427. The first area 401 of the first detector sub-module 42 is stacked, e.g., along Y direction, on the first side surface 426 of the second area 402 of the second detector sub-module 42, so that the detecting devices of the detector sub-modules 42 in the detector module 40 are located on a same side of the detector module 40, that is, a light receiving side facing the radiation source 12.

In the embodiments of the present disclosure, the first area 401 provided with the detecting device of the first detector sub-module 42 at least partially overlaps with the second area 402 having no detection function of the second detector sub-module 42, so that gaps between the detecting devices of adjacent detector sub-modules 42 can be reduced or eliminate as much as possible; thus a relatively complete scanning data of the object can be obtained.

In some embodiments, in the extension direction (Z direction) of the support 41, the first area 401 of the first detector sub-module 42 and the second area 402 of the second detector sub-module 42 are arranged adjacent to each other, the first area of the first detector sub-module 42 can completely cover the second area 402 of the second detector sub-module 42. That is, in adjacent two detector sub-modules 42, the first area 401 of a detector sub-module 42 completely covers with the second area 402 of the other detector sub-module 42. In this way, the detecting devices in the detecting module 40 can be continuously arranged in the Z direction to eliminate the gaps formed by the existence of the functional devices. Such an arrangement can realize continuous scanning data for the object, so that a complete image of the object can be obtained.

In some embodiments, as shown in FIGS. 2 and 3 in combination with FIGS. 6a-6d, the plurality of detector sub-modules 42 are arranged in parallel to each other in a stacking direction, e.g., Y direction, in which the plurality of detector sub-modules are stacked, where a height difference between two sub-modules 42 overlapping with each other is ΔH. Each pair of ones of the plurality of detector submodules 42 can be arranged symmetrical to each other or at least two of the plurality of detector sub-modules 42 are arranged asymmetrical to each other in the extension direction, so that the detector module 40 has an overall symmetrical or asymmetrical step-shaped structure. The stacked detector sub-modules arranged in parallel refers to that the planes where the detector sub-modules 42 are located are arranged parallel to each other. The planes are XZ planes that respectively go through central points of the detector sub-modules 42 in the Y direction.

Figure 6A:
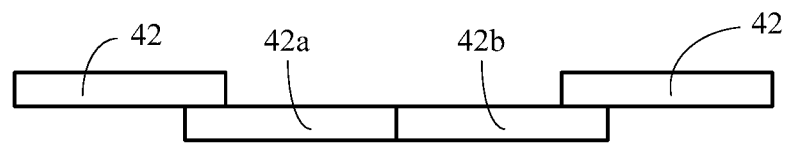
FIGS. 6A to 6G illustrate various arrangements of detector sub-modules according to one or more embodiments of the present disclosure.
Figure 6B:
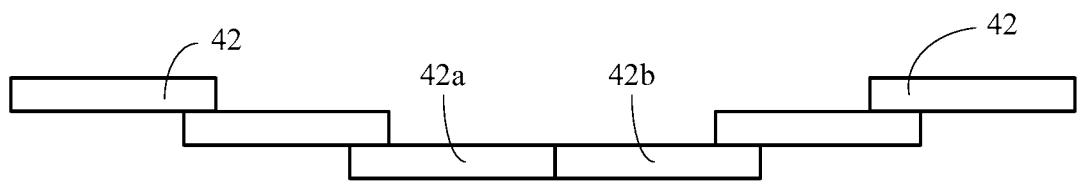
Figure 6C:
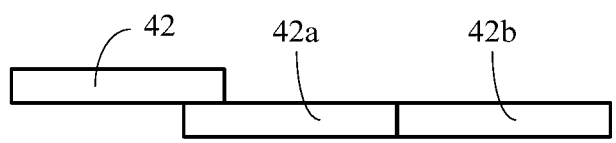
Figure 6D:
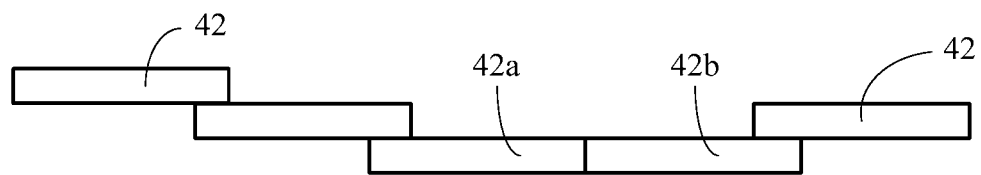
Figure 6E:
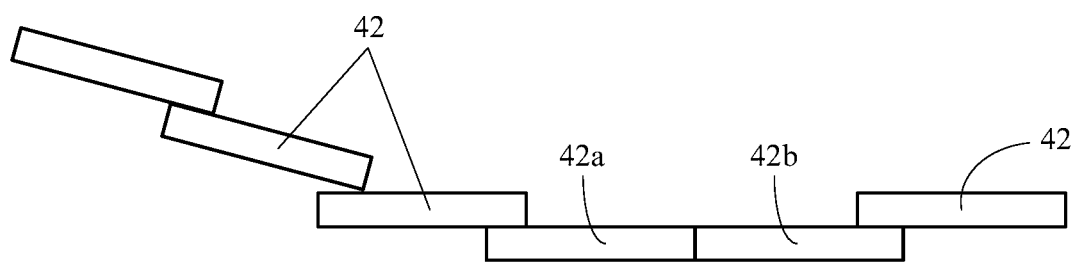
Figure 6F:
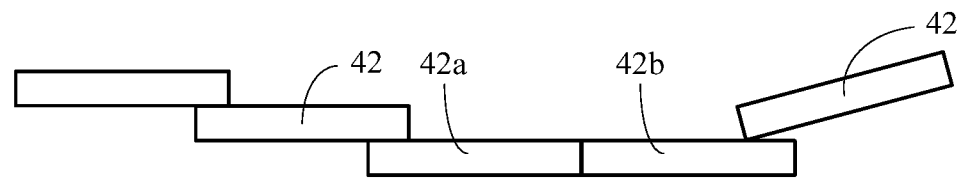
Figure 6G:
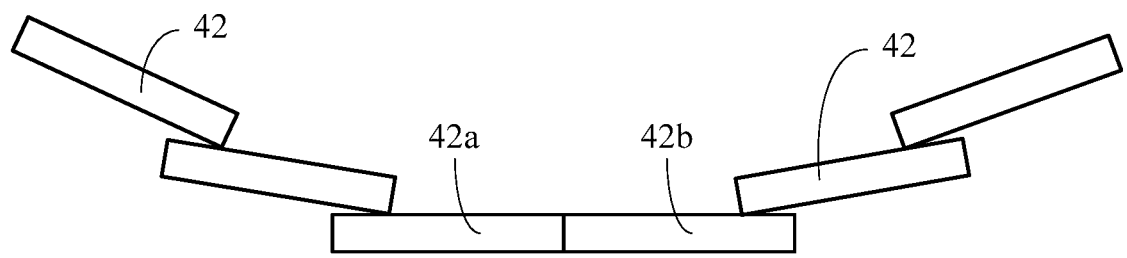

In some embodiments, as shown in FIG. 2 in combination with FIGS. 6E-6G, the first detector sub-module 42 is inclined with respect to the second detector sub-module 42. By obliquely arranging some or all of the overlapping detector sub-modules 42 among the plurality of detector sub-modules, the detector module 40 can receive rays emitted from the radiation source in different angles. The plurality of detector sub-modules 42 can be arranged symmetrically or asymmetrically, so that the detector module 40 can form a curved polyline surface. For example, the detector module 40 can form a stepped curved polyline surface, and the curved polyline surface can be symmetrical or asymmetrical.

In the present disclosure, space is left for the analog-to-digital converter 424 provided on the substrate 421 through the stepped arrangement in the Y direction, while the distances from the focal point of the radiation source to different detector sub-modules 42 of a same detector module 40 can be different. During the subsequent data processing, data detected by the detector sub-modules 42 at different distances in the same detector module 40 can be processed separately, and deviations caused by a traveling path of the X-rays can be corrected according to the distances. In some cases, the medical imaging device 100 can also include a grating arranged on a side that the detector sub-modules 42 receive the rays. Due to the different distances between the focal point of the radiation source and the different detector sub-modules 42 of the same detector module 40, rays received at different detector sub-modules 42 are also different, and the corresponding gratings are designed as gratings of different heights for scattering shielding according to the position of the detector sub-module 42.

Based on the above embodiment, in the present disclosure, among the plurality of detector sub-modules 42, for a third detector sub-module 42a and a fourth detector sub-module 42b located at a bottom layer in the stacking direction, the first area of the third detector sub-module 42a and the first area of the fourth detector sub-module 42b are joined to each other. In a direction from the first area 401 of the third detector sub-module 42a towards the second area 402 of the third detector sub-module 42a, at least one of the plurality of detector sub-modules 42 is stacked at least partially on the third detector sub-module 42a sequentially; and/or in a direction from the first area 401 of the fourth detector sub-module 42b towards the second area 402 of the fourth detector sub-module 42b, at least one of the plurality of detector sub-modules 42 is stacked at least partially on the fourth detector sub-module 42b sequentially. In this embodiment, the third detector sub-module 42a and the fourth detector sub-module 42b are defined as stacking reference detector sub-modules 42, and other detector sub-modules 42 can be sequentially stacked on the third detector sub-module 42a or the fourth detector sub-module 42b to form a stepped structure. The plurality of detector sub-modules 42 can be stacked in a symmetrical or asymmetrical manner and can be arranged as a curved polyline surface as needed.

Referring to FIGS. 6A and 6B, the first area of the third detector sub-module 42a and the first area of the fourth detector sub-module 42b are joined to each other. At least one layer of detector sub-modules 42 are symmetrically stacked on the third detector sub-module 42a and the fourth detector sub-module 42b. For example, in FIG. 6A, one layer of detector sub-module 42 is stacked on each of the third detector sub-module 42a and the fourth detector sub-module 42b. In FIG. 6B, two layers of detector sub-modules 42 can be sequentially stacked on each of the third detector sub-module 42a and the fourth detector sub-module 42b. The number of layers of the detector sub-modules 42 symmetrically stacked is not limited to the present disclosure. Depending on detection requirements, multiple layers of detector sub-modules 42 can be sequentially stacked on the third detector sub-module 42a and the fourth detector sub-module 42b, respectively.

Referring to FIGS. 6C and 6D, the first area 401 of the third detector sub-module 42a and the first area 401 of the fourth detector sub-module 42b are joined to each other. The detector sub-modules 42 can be asymmetrically stacked on the third detector sub-module 42a and the fourth detector sub-module 42b according to a range for receiving the rays. In FIG. 6C, one layer of detector sub-modules 42 is stacked on the third detector sub-module 42a. In some cases, multiple layers of detector sub-modules 42 can also be stacked on the third detector sub-module 42a. In FIG. 6D, two layers of detector sub-modules 42 are sequentially stacked on the third detector sub-module 42a, and one layer of detector sub-module 42 is stacked on the fourth detector sub-module 42b. In some embodiments, the number of layers of the asymmetrically stacked detector sub-modules 42 is not limited to the present disclosure. For example, depending on the detection requirements, one or more layers of detector sub-modules 42 can be sequentially stacked on the third detector sub-module 42a; or one or more layers of detector sub-modules 42 can be sequentially stacked on the fourth detector sub-module 42b.

Referring to FIGS. 6E and 6G, the first area of the third detector sub-module 42a and the first area of the fourth detector sub-module 42b are joined to each other. Among the at least one layer of detector sub-modules 42 stacked on the third detector sub-module 42a and the fourth detector sub-module 42b, some of the detector sub-modules 42 can be inclined with respect to corresponding overlapping detector sub-modules 42. In some embodiments, all of the detector sub-modules 42 stacked on the third detector sub-module 42a and the fourth detector sub-module 42b can be inclined with respect to the corresponding overlapping detector sub-modules 42. In the above embodiment, the detector sub-modules 42 stacked on the third detector sub-module 42a and the fourth detector sub-module 42b can be arranged symmetrically or asymmetrically.

In FIG. 6E, one layer of detector sub-module 42 is stacked on the fourth detector sub-module 42b, and three layers of detector sub-modules 42 are sequentially stacked on the third detector sub-module 42a. A second layer of the stacked detector sub-modules 42 on the third detector sub-module 42a is inclined with respect to a first layer of the stacked detector sub-modules 42. In this way, the angle at which the detector module 40 receives the rays can be adjusted, which contributes to the detection of the rays by the detector module 40. In some cases, the detector module 40 is not limited to the arrangement shown in the FIGS. 6A-6E. Arrangements in which the plurality of detector sub-modules 42 are partially stacked in parallel and partially inclined are all applicable to this disclosure.

In FIG. 6F, two layers of detector sub-modules 42 are sequentially stacked on the third detector sub-module 42a, and one layer of detector sub-module 42 is inclined with respect to the fourth detector sub-module 42b. In this way, the angle at which the detector module 40 receives the rays can be adjusted, which contributes to the detection of the rays by the detector module 40. In some cases, the detector module 40 is not limited to the arrangement shown in the FIG. 6F. Arrangements in which the plurality of detector sub-modules 42 are partially stacked in parallel and partially inclined are all applicable to this disclosure.

Figure 7A:
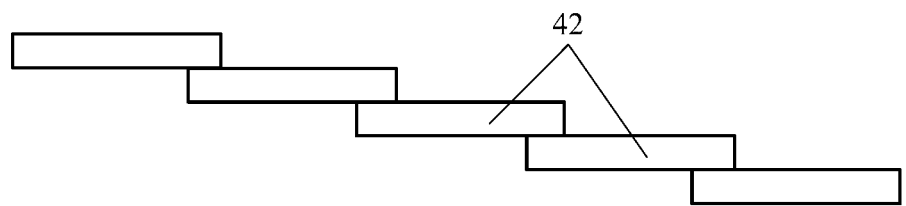
FIGS. 7A and 7B illustrate other two arrangements of detector sub-modules according to one or more embodiments of the present disclosure.
Figure 7B:
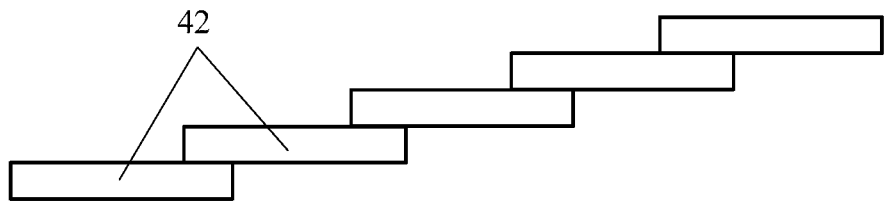

In FIG. 6G, two layers of detector sub-modules 42 are inclined with respect to the third detector sub-module 42a in sequence, and two layers of detector sub-modules 42 are obliquely arranged on the fourth detector sub-module 42b in sequence, so that the detector module 40 can form a symmetrical curved polyline surface structure. In this way, the angle at which the detector module 40 receives the rays can be adjusted, which contributes to the detection of the rays by the detector module 40. In some cases, the number of layers of the stacked detector sub-modules 42 in the detector module 40 is not limited to the present disclosure. In addition, the detector module 40 can also be set to include an asymmetric number of layers of detector sub-modules 42 or asymmetrically detector sub-modules 42 that are inclined to each other to form a curved polyline surface structure. In another embodiment of the present disclosure, referring to FIGS. 7A and 7B, the plurality of detector sub-modules 42 can be sequentially stacked in the Z direction or a direction opposite to the Z direction, so that the first area 401 of each detector sub-module 42 is stacked on the second area 402 of an adjacent detector sub-module 42.

Referring to FIGS. 4 and 5, to protect the analog-to-digital converter 424, X-ray irradiation on the analog-to-digital converter 424 needs to be prevented; thus the detector sub-module 42 can include a shield 43 provided in the second area 402. The shield 43 covers the functional module. In this embodiment, the shield 43 covers the analog-to-digital converter 424. Optionally, the shield 43 is a tungsten sheet. In some cases, the shield 43 is not limited to a tungsten sheet, other metal sheets with protective functions are applicable to the present disclosure.

In addition, because the analog-to-digital converter 424 generates a large amount of heat, in the present disclosure, the analog-to-digital converter 424 of a detector sub-module 42 can be stacked on and at least partially overlapped with the detecting device of another detector sub-module 42, the detector sub-module 42 can include a thermally conductive adhesive 44 provided between the functional module and the shield 43. The thermally conductive adhesive 44 can speed up the heat dissipation of the detector sub-module 42 and slow down the heat conduction from the analog-to-digital converter 424 to the detecting device stacked thereon.

As shown in FIG. 2, the detector module 40 of the present disclosure can include a thermal fin 45 disposed on the support 41. The thermal fin 45 and the detector sub-modules 42 are disposed on two opposite sides of the support 41, respectively. At least part of the thermal fin 45 is provided with a gradually increasing heat dissipation area in a heat dissipation wind direction. The heat dissipation wind direction is consistent with the extension direction of the support 41, and the heat dissipation area is the cross-sectional area of the thermal fin 45 along a plane perpendicular to the heat dissipation wind direction. In this embodiment, the thermal fin 45 can be designed as a form of single side cut, hollow or of unequal height or unequal thickness, etc., so as to achieve the heat balance of the support 41 after heat dissipation and reduce the temperature difference between the detector sub-modules 42.

Figure 8:
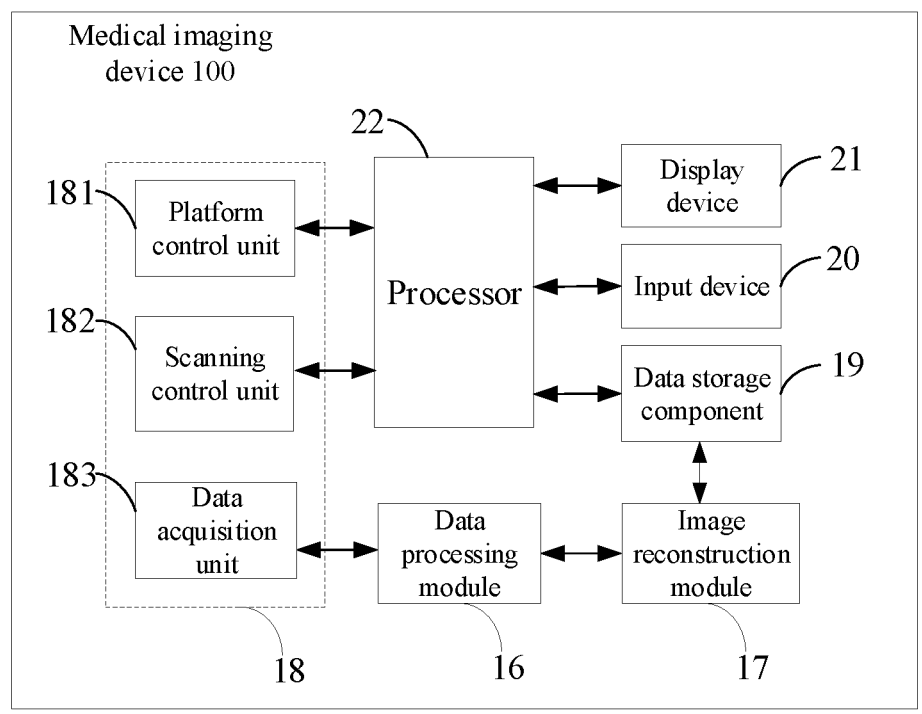
FIG. 8 illustrates a block diagram of a medical imaging device according to one or more embodiments of the present disclosure.

As shown in FIG. 8 in combination with FIG. 1A, the medical imaging device 100 can include a control module 18. The control module 18 includes a platform control unit 181, a scanning control unit 182 and a data acquisition unit 183.

The platform control unit 181 controls the movement of the platform 15. The scanning control unit 182 controls a rotation speed and angular orientation of the radiation source 12 and the detector 13. The data acquisition unit 183 is connected to the detector 13 for collecting digital signals generated by the detector 13 and provide the digital signals to a data processing module 16.

The data processing module 16 is used to process the data corresponding to the electrical signals generated by the detector sub-modules 42 located on circles of different radii in a same detector module 40; according to the different radii, correct data difference produced by different paths that the rays passing through; and correct noise difference of different detector sub-modules 42. The data processing module 16 then provides the processed data to an image reconstruction module 17, and the image reconstruction module 17 reconstructs the image according to the data processed by the data processing module 16.

The image reconstructed by the image reconstruction module 17 can be stored in a data storage component 19. In some embodiments, the data storage component 19 can also store intermediate processing data generated during the image reconstruction process. In some embodiments, the data storage component 19 can be a magnetic storage medium or an optical storage medium, such as a hard disk, a storage chip, etc., but is not limited thereto.

In some embodiments, the medical imaging device 100 can further include an input device 20 and a display device 21. The input device 20 is used to receive input from users and can include a keyboard and/or other user input devices. The display device 21 can display the reconstructed image and/or other data. The display device 21 can include a liquid crystal display, a cathode ray tube display, a plasma display, and the like.

In some embodiments, the medical imaging device 100 further includes a processor 22. The processor 22 can receive instructions and scanning parameters input through the input device 20. The processor 22 can provide control signals and information to the platform control unit 181, the scanning control unit 182, and the data acquisition unit 183.

The data processing module 16, the image reconstruction module 17, the control module 18, and the processor 22 of the medical imaging device 100 can be implemented by software, hardware or a combination of software and hardware. The medical imaging device 100 can also include other elements not shown. The device embodiments described above are merely illustrative. The units described as separate components can or can not be physically separated, and the components displayed as units can or can not be physical units, that is, they can be located in one place, or they can be distributed to multiple network units. Some or all of the parts thereof can be selected according to actual needs to achieve the purpose of the present disclosure.

In the present disclosure, a plurality of detector sub-modules are arranged in a stepped stacking structure along a Y direction, and a functional module in a second area is at least partially blocked by a detecting device in a first area. As such, non-detection gaps between two adjacent detector sub-modules are reduced. Accordingly, more detector submodules can be stacked in a Z direction to produce a larger detection coverage area, which makes the detector sub-modules more widely used. In addition, the joining method for the detector sub-modules is more flexible, therefore the detector sub-modules can be applied in CT products with more layers such as 64-slice CT, 128-slice CT, etc.

The present disclosure described in detail with reference to specific embodiments shown in the drawings. However, these embodiments do not limit the present disclosure, and the structural, method, or functional changes made by those skilled in the art according to these embodiments are all included in the protection scope of the present disclosure.

The terms used in the present disclosure are only for the purpose of describing particular embodiments, and is not intended to limit the present disclosure. The singular forms "a", "said" and "the" used in the present disclosure and the appended claims are also intended to include the majority forms unless the context clearly indicates other meanings. It should also be understood that the term "and/or" as used herein refers to and includes any or all possible combinations of one or more associated items listed.

Other embodiments of the present disclosure will readily occur to those skilled in the art upon consideration of the description and practice of the present disclosure. The present disclosure is intended to cover any variation, use or adaptive variation of the present disclosure that follows the general principles of the present disclosure and includes common general knowledge or customary technical means in the art not disclosed in the present disclosure.

It should be understood that the present disclosure is not limited to the precise structures already described above and shown in the drawings, and various modifications and changes can be made without departing from the scope thereof. The scope of the present disclosure is defined by the claims only.

What is claimed is:

1. A detector module, comprising:
a support extending in an extension direction; and
a plurality of detector sub-modules arranged on the support in the extension direction,
wherein each detector sub-module of the plurality of detector sub-modules has a first area and a second area in the extension direction, wherein each detector sub-module of the plurality of detector sub-modules has a substrate with a first part located in the first area and a second part located in the second area, wherein a detecting device is disposed on the first part of the substrate in the first area, wherein a functional module is disposed on the second part of the substrate in the second area,
wherein the detecting device includes a photodiode array and a scintillation crystal array, wherein the functional module includes an analog-to-digital converter and a connector,
wherein the functional module is electrically connected to the detecting device for receiving an electrical signal from the detecting device,
wherein the analog-to-digital converter and the detecting device are disposed on a same side of the substrate and are electrically connected to each other, wherein the analog-to-digital converter and the connector are disposed on opposite sides of the second part of the substrate and are in communication connection via the substrate,
wherein the plurality of detector sub-modules comprises a first detector sub-module and a second detector sub-module that are arranged adjacent to each other in the extension direction, the first area of the first detector sub-module at least partially overlapping with the second area of the second detector sub-module,
wherein each detector sub-module of the plurality of detector sub-modules further comprises a shield disposed over the functional module in the second area of the detector sub-module, and
wherein each detector sub-module of the plurality of detector sub-modules further comprises a thermally conductive adhesive disposed between the functional module and the shield.

2. The detector module of claim 1, wherein the first area of the first detector sub-module completely covers the second area of the second detector sub-module.

3. The detector module of claim 1, wherein the plurality of detector sub-modules are arranged in parallel to each other in a stacking direction in which the plurality of detector sub-modules are stacked.

4. The detector module of claim 1, wherein the first detector sub-module is inclined with respect to the second detector sub-module.

5. The detector module of claim 1, wherein each pair of detector sub-modules of the plurality of detector sub-modules are arranged symmetrical to each other in the extension direction.

6. The detector module of claim 1, wherein at least two of the plurality of detector sub-modules are arranged asymmetrical to each other in the extension direction.

7. The detector module of claim 1, wherein the plurality of detector sub-modules comprise a third detector sub-module and a fourth detector sub-module that are located at a bottom layer in a stacking direction in which the plurality of detector sub-modules are stacked, and the first area of the third detector sub-module and the first area of the fourth detector sub-module are joined to each other.

8. The detector module of claim 1, further comprising a thermal fin,
wherein the thermal fin and the plurality of detector sub-modules are respectively disposed on opposite sides of the support.

9. The detector module of claim 1, wherein the substrate is configured to electrically connect the functional module to the detecting device and transmit the electrical signal generated by the detecting device to the functional module.

10. The detector module of claim 1, wherein a first detecting device in the first area of the first detector sub-module is higher than a second detecting device in the first area of the second detector sub-module along a stacking direction in which the plurality of detector sub-modules are stacked, and wherein detecting devices in first areas of at least two of the plurality of detector sub-modules are arranged at a same height along the stacking direction.

11. The detector module of claim 7, wherein at least one of the plurality of detector sub-modules is stacked at least partially on the third detector sub-module sequentially in a direction from the first area of the third detector sub-module to the second area of the third detector sub-module.

12. The detector module of claim 7, wherein at least one of the plurality of detector sub-modules is stacked at least partially on the fourth detector sub-module sequentially in a direction from the first area of the fourth detector sub-module to the second area of the fourth detector sub-module.

13. The detector module of claim 8, wherein at least part of the thermal fin is provided with a gradually increasing heat dissipation area in a heat dissipation wind direction.

14. A detector, comprising:
a housing; and a plurality of detector modules arranged in parallel on the housing, each of the detector modules comprising:
  a support extending in an extension direction; and
  a plurality of detector sub-modules arranged on the support along the extension direction,
wherein the plurality of detector modules are arranged in parallel in a stacking direction,
wherein the extension direction and the stacking direction are perpendicular to each other and are both perpendicular to a direction in which rays are received,
wherein each detector sub-module of the plurality of detector sub-modules has a first area and a second area in the extension direction, wherein each detector sub-module of the plurality of detector sub-modules has a substrate with a first part located in the first area and a second part located in the second area, wherein a detecting device is disposed on the first part of the substrate in the first area, wherein a functional module is disposed on the second part of the substrate in the second area,
wherein the detecting device includes a photodiode array and a scintillation crystal array, wherein the functional module includes an analog-to-digital converter and a connector,
wherein the functional module is electrically connected to the detecting device for receiving an electrical signal from the detecting device,
wherein the analog-to-digital converter and the detecting device are disposed on a same side of the substrate and are electrically connected to each other, wherein the analog-to-digital converter and the connector are disposed on opposite sides of the second part of the substrate and are in communication connection via the substrate,
wherein the plurality of detector sub-modules comprises a first detector sub-module and a second detector sub-module that are arranged adjacent to each other in the extension direction, the first area of the first detector sub-module at least partially overlapping with the second area of the second detector sub-module,
wherein each detector sub-module of the plurality of detector sub-modules further comprises a shield disposed over the functional module in the second area of the detector sub-module, and
wherein each detector sub-module of the plurality of detector sub-modules further comprises a thermally conductive adhesive disposed between the functional module and the shield.

15. The detector of claim 14, wherein a first detecting device in the first area of the first detector sub-module is higher than a second detecting device in the first area of the second detector sub-module along the stacking direction, and wherein detecting devices in first areas of at least two of the plurality of detector sub-modules are arranged at a same height along the stacking direction.

16. A medical imaging device, comprising:
a scanner gantry formed with an opening for receiving an object to be scanned;
a radiation source for emitting rays to the object; and
a detector configured to receive the rays attenuated through the object and convert the attenuated rays into electrical signals,
wherein the detector and the radiation source are disposed respectively on opposite sides of the opening of the scanner gantry,
wherein the detector comprises:
  a housing; and
  a plurality of detector modules arranged in parallel on the housing, wherein each of the detector modules comprises:
    a support extending in an extension direction; and
    a plurality of detector sub-modules arranged on the support along the extension direction,
wherein the plurality of detector modules are arranged in parallel in a stacking direction,
wherein the extension direction and the stacking direction are perpendicular to each other and are both perpendicular to a direction in which the rays are received,
wherein each detector sub-module of the plurality of detector sub-modules has a first area and a second area in the extension direction, wherein each detector sub-module of the plurality of detector sub-modules has a substrate with a first part located in the first area and a second part located in the second area, wherein a detecting device is disposed on the first part of the substrate in the first area, wherein a functional module is disposed on the second part of the substrate in the second area,
wherein the detecting device includes a photodiode array and a scintillation crystal array, wherein the functional module includes an analog-to-digital converter and a connector,
wherein the functional module is electrically connected to the detecting device for receiving an electrical signal from the detecting device,
wherein the analog-to-digital converter and the detecting device are disposed on a same side of the substrate and are electrically connected to each other, wherein the analog-to-digital converter and the connector are disposed on opposite sides of the second part of the substrate and are in communication connection via the substrate,
wherein the plurality of detector sub-modules comprises a first detector sub-module and a second detector sub-module that are arranged adjacent to each other in the extension direction, the first area of the first detector sub-module at least partially overlapping with the second area of the second detector sub-module,
wherein each detector sub-module of the plurality of detector sub-modules further comprises a shield disposed over the functional module in the second area of the detector sub-module, and
wherein each detector sub-module of the plurality of detector sub-modules further comprises a thermally conductive adhesive disposed between the functional module and the shield.

17. The medical imaging device of claim 16, wherein a first detecting device in the first area of the first detector sub-module is higher than a second detecting device in the first area of the second detector sub-module along the stacking direction, and wherein detecting devices in first areas of at least two of the plurality of detector sub-modules are arranged at a same height along the stacking direction.

* * * * *